(12) United States Patent
Yoon et al.

(10) Patent No.: US 7,115,655 B2
(45) Date of Patent: Oct. 3, 2006

(54) PYRANOCOUMARIN DERIVATIVES

(75) Inventors: Jeong-Seon Yoon, Eumseong-gun (KR); Ji-Young Lee, Seoul (KR); Young-Choong Kim, Seoul (KR); Ki-Yong Lee, Kumi-shi (KR); Sang-Hyun Sung, Seoul (KR); Hak-Joong Kim, Seoul (KR); So-Young Kang, Seoul (KR)

(73) Assignee: Elcom Biotechnology, Co. Ltd., Seoul (KR)

( * ) Notice: Subject to any disclaimer, the term of this patent is extended or adjusted under 35 U.S.C. 154(b) by 6 days.

(21) Appl. No.: 10/510,923

(22) PCT Filed: Apr. 9, 2002

(86) PCT No.: PCT/KR02/00627

§ 371 (c)(1),
(2), (4) Date: Oct. 8, 2004

(87) PCT Pub. No.: WO03/087082

PCT Pub. Date: Oct. 23, 2003

(65) Prior Publication Data

US 2005/0222245 A1    Oct. 6, 2005

(51) Int. Cl.
*A61K 31/35* (2006.01)
(52) U.S. Cl. .................................. 514/455; 549/282
(58) Field of Classification Search ................ 514/455; 549/282
See application file for complete search history.

(56) References Cited

FOREIGN PATENT DOCUMENTS

| WO | WO 00/23074 | 4/2000 |
|---|---|---|
| WO | WO 01/52841 | 7/2001 |

OTHER PUBLICATIONS

Konoshima, Masao et al 'Coumarins from the root of *Angelica gigas*' CA 69:103778 (1968).*
Ringman, Metrifonate: update on a new antidementia agent, PMID: 10584768.*
Doody, Clinical benefits of a new piperidine-clas AchE inhibitor, PMID: 10332937.*
Kang, S.Y. et al. "Coumarins Isolated from *Angelica gigas* Inhibit Acetylcholinesterase: Structure—Activity Relationships", *J. Nat. Prod.* (2001) 64:683-685.

* cited by examiner

*Primary Examiner*—Amelia A. Owens
(74) *Attorney, Agent, or Firm*—Greenlee Winner and Sullivan PC

(57) ABSTRACT

The present invention relates to compounds of the following formula (I) or pharmaceutically acceptable salts thereof. The present invention also relates to use for a cognitive-enhancing agent of compounds of the following formula (I) or pharmaceutically acceptable salts thereof and to a process for preparing the same. Further, the present invention relates to use for a congnitive-enhancing agent of decursin of the following formula (II) or pharmaceutically acceptable salts thereof. In addition, the present invention relates to extracts of *Angelica gigantis* Radix comprising decursin of the following formula (II), having cognitive-enhancing effects.

5 Claims, No Drawings

PYRANOCOUMARIN DERIVATIVES

CROSS REFERENCE TO RELATED APPLICATIONS

This application is a National Stage Agpplication of Patent Cooperation Treaty International Application PCT/KR02/00627, filed 9 Apr. 2002.

TECHNICAL FIELD

The present invention relates to pyranocoumarin derivatives having the following general formula:

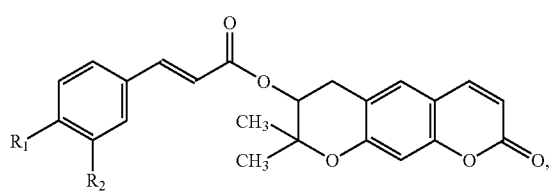

(I)

wherein $R_1$ and $R_2$ each represent hydrogen or $C_{1-4}$alkoxy, or pharmaceutically acceptable salts thereof.

BACKGROUND ART

Senile dementia has recently been recognized as a degenerative central nerve system disorder. The number of patients suffering from the disease has been increased to become a serious social problem, and so the prevention, amelioration, and treatment of the disease are now considered very important.

Alzheimer's disease, vascular diseases, Parkinson's disease, hypothyroidism, and alcoholic dementia are known as disorders which may cause dementia, but more than 50% of the patients suffering from senile dementia are found to suffer from Alzheimer's disease. The central nerve system of the patients suffering from Alzheimer's disease is generally impaired, and particularly, cholinergic neuron is most severely impaired. Thus, the studies to develop therapeutic agents to improve cholinergic neuronal functions have been vigorously conducted.

A method to improve the functions of impaired cholinergic neuron is to administer cholinergic receptor agonist or acetylcholinesterase (AChE) inhibitor to inhibit degradation of acetylcholine (ACh), a cholinergic neurotransmitter, and thereby to maintain the concentration of synaptic ACh.

However, cholinergic receptor agonist has a disadvantage to be readily degraded in vivo, and thus, AChE inhibitor is generally used. That is, AChE inhibitor ameliorates the conditions of senile dementia by preventing the degradation of AChE by inhibiting the activity of AChE, an enzyme to degrade ACh, and maintaining the concentration of synaptic Ach, and thereby sustaining a series of cholinergic receptor-mediated reactions.

This is supported by the fact that most of the drugs that have been developed as therapeutic agents for Alzheimer's disease and currently on clinical use or trial are AChE inhibitors. AChE inhibitors that have been approved by the United States Food and Drug Administration and used as therapeutic agents of dementia are exemplified by tacrine (THA, Cognex®), donepezil (Aricept®), rivastigmaine (Exelon®), and galanthamine (Reminyl®) that is most recently approved. However, these AChE inhibitors are known to have such problems as hepatotoxicity, short half-life, low bioavailability, etc. Thus, more studies have been performed to develop a novel AChE inhibitor.

The present inventors have tested various natural products for AChE inhibitory activity to identify the activity with using in vivo experimental models by finding a substance with AChE inhibitory activity from the natural products that have been used as traditional Korean folk medicines for a long time. As a result, the present inventors found out that a methanolic extract of *Angelicae gigantis* Radix has significant AChE inhibitory activity and cognition-enhancing activity.

*Angelicae gigantis* Radix is an herbal medicine used as a sedative, an analgesic, or a tonic agent, and particularly an essential drug used after childbirth for anemia and women's diseases, etc. by sedative and menstruation-promoting actions. In Korea, the dried root of *Angelica gigas* Nakai has been used as *Angelicae gigantis* Radix.

Further, the present inventors isolated and purified active ingredients showing AChE inhibitory and cognition-enhancing activities from *Angelicae gigantis* Radix, and synthesized many compounds by using the active ingredients as starting materials and tested them for their cognition-enhancing activity. As a result, they found out pyranocoumarin derivatives of the general formula (I) have cognition-enhancing activity. Therefore, the present inventors completed the present invention.

DISCLOSURE OF THE INVENTION

The present invention provides pyranocoumarin derivatives of the following general formula:

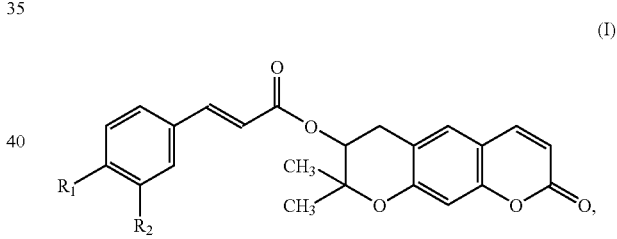

(I)

wherein $R_1$ and $R_2$ each represent hydrogen or $C_{1-4}$alkoxy, or pharmaceutically acceptable salts thereof.

The present invention also provides an agent for enhancing cognition, comprising the compounds of the above general formula (I) or pharmaceutically acceptable salts thereof.

The present invention further provides a process for preparing the compounds of the above general formula (I).

The present invention still further provides an agent for enhancing cognition, comprising decursin of the following formula:

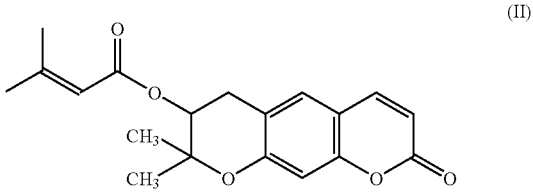

(II)

or a pharmaceutically acceptable salt thereof as an active ingredient.

The present invention still further provides an extract of *Angelicae gigantis* Radix, comprising decursin of the above formula (II).

Hereinafter, the present invention will be explained in detail.

One aspect of the present invention provides novel compounds of the general formula:

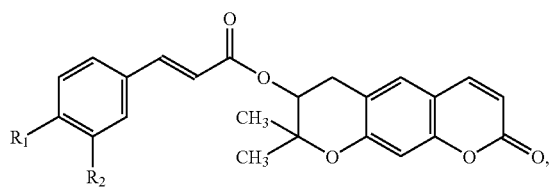

(I)

wherein $R_1$ and $R_2$ each represent hydrogen or $C_{1-4}$alkoxy, and preferably, $R_1$ is $OCH_3$, and $R_2$ is hydrogen.

Another aspect of the present invention provides a process for preparing the compounds of the general formula (I) by conventional esterification reaction of decursinol (a) with phenyl propanoids (b), as depicted in the following reaction scheme:

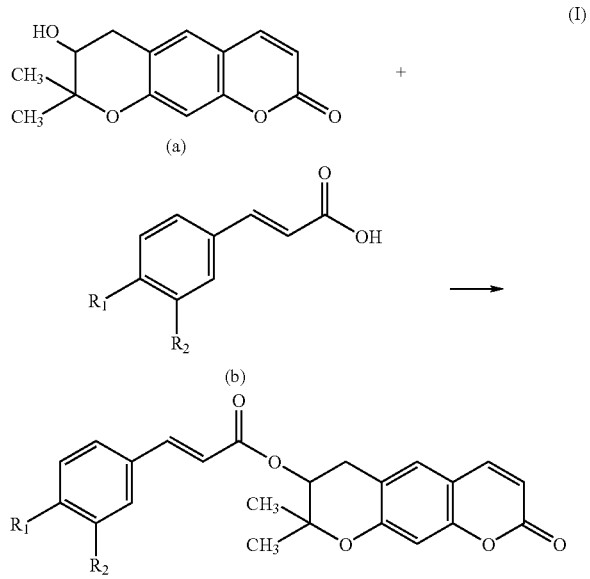

The starting material, decursinol (a), may be prepared by direct extraction of *Angelicae gigantis* Radix, or by alkaline hydrolysis of decursin of the above formula (II), one ingredient of *Angelicae gigantis* Radix.

The present inventors first confirmed that decursin of formula (II), one ingredient of *Angelicae gigantis* Radix, has cognition-enhancing activity, synthesized many compounds using the ingredients of *Angelicae gigantis* Radix as starting materials, and screened the compounds for their cognition-enhancing activity. As a result, the present inventors found that the compounds of the general formula (I) have superior cognition-enhancing activity.

A third aspect of the present invention provides an agent for enhancing cognition, comprising the compounds of the general formula (I) as an active ingredient.

The compounds of the general formula (I) according to the present invention can be formulated according to methods known in pharmaceutical field. The compounds alone or in admixture with pharmaceutically acceptable carriers, excipients, etc. are manufactured into conventional pharmaceutically acceptable dosage forms, for example, injectable formulations, solutions, syrups, tablets, capsules and the like. The compounds of the general formula (I) according to the present invention may be converted into pharmaceutically acceptable inorganic or organic salts using conventional pharmaceutical methods. They may be administered by oral or parenteral route.

The dose of the compounds of the general formula (I) according to the present invention may be appropriately selected depending upon absorption rate and excretion rate of the active ingredient, patient's age, body weight, sexuality and condition, and severity of disease to treat, and generally, their daily dose is in the range of 0.01 to 500 mg/kg, and preferably, 0.1 to 200 mg/kg to an adult. The compounds of formula (I) of the present invention may be administered several times with a regular interval, if necessary.

A fourth aspect of the present invention provides an agent for enhancing cognition, comprising decursin of the above formula (II) as an active ingredient.

Decursin of the present invention may be extracted from *Angelicae gigantis* Radix, or synthesized using conventional methods. One example of the extraction method of *Angelicae gigantis* Radix in the present invention is as follows.

The root of *Angelica gigas* Nakai is extracted with $C_{1-4}$alcohol, for example, methanol, ethanol, propanol, etc., and the obtained extract is suspended in water, and then, partitioned with dichloromethane ($CH_2Cl_2$) to obtain water fraction and dichloromethane fraction. The dichloromethane fraction is further purified by column chromatography on silica gel (for example, using n-hexane:$CHCl_3$:MeOH as an eluent), and recrystallized to obtain decursin.

The above extract of *Angelicae gigantis* Radix and decursin according to the present invention have excellent cognition-enhancing activity.

Decursin and extract of *Angelicae gigantis* Radix according to the present invention may be formulated according to methods known in pharmaceutical field, and decursin of the present invention may be converted into pharmaceutically acceptable inorganic or organic salts thereof according to conventional pharmaceutical methods.

Doses of decursin and *Angelica gigantis* Radix extract of the present invention are generally in the range of 0.01 to 500 mg/kg, and preferably, 0.1 to 200 mg/kg a day to an adult. The extract of *Angelicae gigantis* Radix according to the present invention may be administered at 0.01 to 500 mg once to three times a day, and decursin of the present invention may be administered at 0.1 to 200 mg once to three times a day.

As used herein, the term "*Angelicae gigantis* Radix" means the root of *Angelica gigas*, the term "$C_{1-4}$alcohol" means methanol, ethanol, propanol, isopropanol or butanol, for example, and the term "$C_{1-4}$alkoxy" means methoxy, ethoxy, propoxy, isopropoxy or butoxy, for example.

BEST MODE FOR CARRYING OUT THE INVENTION

The present invention will be more specifically illustrated by the following examples. However, the following examples should not be construed to limit the scope of the present invention.

EXAMPLE 1

Extraction and Fractionation of *Angelicae gigantis* Radix

The dried root of *Angelica gigas* (5 kg) was finely powdered, and extracted with MeOH in an ultrasonic apparatus to obtain a methanolic extract (350 g). The extract was suspended in water, and partitioned with $CH_2Cl_2$ to obtain $CH_2Cl_2$ fraction (220 g).

EXAMPLE 2

Isolation and Structural Identification of Decursin from the Extract of *Angelicae gigantis* Radix The $CH_2Cl_2$ fraction of *Angelica gigas* obtained in Example 1 was subjected to column chromatography on silica gel (n-hexane:$CHCl_3$:MeOH) to obtain 7 fractions (AG-C-01 to 07). A part of AG-C-03 of those fractions was recrystallized with EtOH to isolate 678 mg of Compound 1. The compound emitted purple fluorescence at UV of long wavelength (365 nm), and developed purple color with anisaldehyde-$H_2SO_4$.

Compound 1:
Colorless prism
$C_{19}H_{20}O_5$
EIMS (m/z) (rel. int.): 328[M]$^+$ (0.7), 228 (21.4), 213 (100.0), 83 (24.7), 55 (20.1)
$^1$H NMR (300 MHz, CDCl$_3$): δ 1.31 (3H, s, C$\underline{H}_3$2'), 1.33 (3H, s, C$\underline{H}_3$2'), 1.83 (3H, d, J=1.2 Hz, CH$_3$-4"), 2.09 (3H, d, J=1.2 Hz, C$\underline{H}_3$-3"), 2.85 (1H, dd, J=4.9, 17.3 Hz, H-4'), 3.18 (1H, dd, J=4.9, 17.3 Hz, H-4'), 5.04 (1H, t, J=4.9 Hz, H-3'), 5.61 (1H, m, H-2"), 6.19 (1H, d, J=9.5 Hz, H-3), 6.74 (1H, s, H-5), 7.11 (1H, s, H-8), 7.56 (1H, d, J=9.5 Hz, H-4) ppm
$^{13}$C NMR (75 MHz, CDCl$_3$): δ 20.3 (3"-CH$_3$), 23.1 (2'-CH$_3$), 25.0 (2'-CH$_3$), 27.5 (C-4"), 27.9 (C-2'), 69.1 (C4'), 76.6 (C-3'), 104.7 (C-8'), 112.8 (C-10'), 113.2 (C-3), 115.5 (C-2"), 115.9 (C-6), 128.6 (C-5), 143.1 (C-4), 154.1 (C-9), 156.4 (C-7), 158.5 (C-3"), 161.3 (C-2), 165.7 (C-1")

Chemical formula:

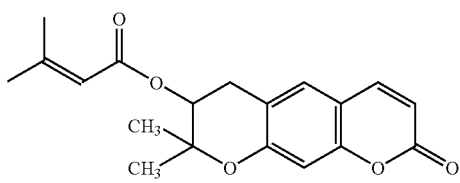

Compound 1 was identified as decursin by comparing the above physicochemical properties and spectroscopic results with those in the literature (Ahn, K. S. et al. (1996) Decursin: A cytotoxic agent and protein kinase C activators from the root of *Angelica gigas*, Planta Med. 62: 7–9).

EXAMPLE 3

Preparation of Pyranocoumarin Derivatives of the General Formula (I)

(1) Alkaline Hydrolysis of Decursin

Decursin of 1 g obtained from Example 2 was dissolved in 40 ml of 5% ethanolic KOH, and a reaction was performed at 60° C. for 1 hour. The reaction mixture was cooled and thereto was added water to terminate the reaction. Then, the reaction mixture was partitioned with ethyl acetate. The fraction was concentrated and recrystallized with chloroform to obtain Compound 2 (680 mg).

Compound 2 emitted blue fluorescence at UV of long wavelength (365 nm), and developed purple color with anisaldehyde-$H_2SO_4$.

Compound 2:
$C_{14}H_{14}O_4$
Colorless needles
EIMS (m/z) (rel. int.): 246 [M]$^+$
$^1$H NMR (300 MHz, CDCl$_3$): δ 1.34 (3H, s, gem-CH$_3$), 1.37 (3H, s, gem-CH$_3$), 2.81 (1H, m, H-4'), 3.09 (1H, m, H-4'), 3.85 (1H, t, J=5.0 Hz, H-3'), 6.20 (1H, d, J=9.5 Hz, H-3), 6.76 (1H, s, H-5), 7.16 (1H, s, H-8), 7.56 (1H, d, J=9.5 Hz, H-4) ppm
$^{13}$C NMR (75 MHz, CDCl$_3$): δ 22.0 (gem-CH$_3$), 25.0 (gem-CH$_3$), 30.6 (C-2'), 69.1 (C4'), 78.1 (C-3'), 104.7 (C-8), 112.9 (C-10), 113.3 (C-3'), 116.4 (C-6 ), 182.9 (C-5), 143.1 (C4), 154.1 (C-9), 156.4 (C-7), 161.2 (C-2) ppm Compound 2 was identified as decursinol by comparing the above physicochemical properties and spectroscopic results with those in the literatures (Konoshima et al. (1968) Coumarins from the root of *Angelica gigas* Nakai. Chem. Pharm. Bull. 16: 1139–1140; and Seong et al. (1988) Studies on the constituents of the roots of *Angelica flaccida* Kommarov. Kor. J. Pharmacogn. 19: 233–238).

(2) Synthesis and Isolation of Compound 3

As depicted in the following reaction scheme, Compound 2(a) obtained from the above (1) of 246 mg (1 mmol), p-methoxycinnamic acid (c) of 356 mg (2 mmol), and 4-(dimethylamino)-pyridine (DMAP) of 122 mg (1 mmol) were dissolved in 10 ml of anhydrous dichloromethane, and a reaction was performed under nitrogen at room temperature for 5 minutes. Then, 1,3-dicyclohexyl carbodiimide (DCC) of 300 mg (1.5 mmol) was added thereto, and the reaction was further performed for 2 hours. The reaction mixture was cooled and filtered through Celite 545, and then, the filtrate was subjected to column chromatography on silica gel (hexene:ethyl acetate=2:1) to isolate Compound 3 (250 mg).

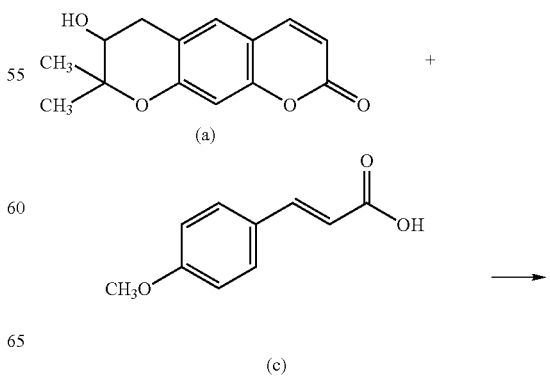

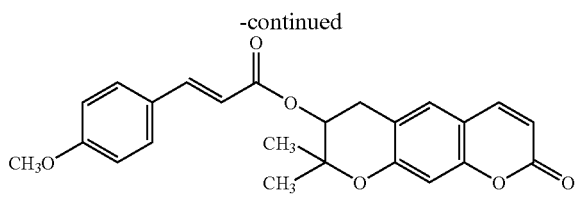

(3) Structural Identification of Compound 3

$C_{24}H_{22}O_6$

EIMS (m/z): 406 [M]$^+$, 246 [M-160]$^+$ $^1$H NMR (300 MHz, CD$_3$OD): δ 1.28 (3H, s, gem-CH$_3$), 1.30 (3H, s, gem-CH$_3$), 2.84 (1H, dd, J=17.5, 4.6 Hz, H$_\alpha$-4'), 3.18 (1H, dd, J=18.4, 4.6 Hz, H$_\beta$-4'), 3.69 (3H, s, OCH$_3$), 3.99 (1H, q, J=7.1 Hz, H-3'), 6.10 (1H, d, J=9.5 Hz, H-3), 6.10 (1H, d, J=15.84 Hz, H-7''), 6.64 (1H, s, H-5), 6.80 (2H, d, J=8.9 Hz, H-3'', 5''), 7.24 (1H, s, H-8), 7.39 (2H, d, J=8.9 Hz, H-2'', 6''), 7.50 (1H, d, J=15.84 Hz, H-8''), 7.69 (1H, d, J=9.5 Hz, H-4) ppm $^{13}$C NMR (75 MHz, CDCl$_3$): δ 22.0 (gem-CH$_3$), 23.8 (gem-CH$_3$), 27.3 (C-2'), 54.4 (OCH$_3$), 70.0 (C4'), 76.7 (C-3'), 103.6 (C-8), 112.1 (C-3), 112.9 (C-10), 114.0 (C-3'', 5''), 114.1 (C-7''), 116.3 (C-6), 126.7 (C-1''), 129.1 (C-5), 129.7 (C-4'', 6''), 144.1 (C-4), 145.4 (C-8''), 153.9 (C-9), 156.6 (C-7, 4''), 161.8 (C-2), 166.6 (C-9'') ppm Chemical formula:

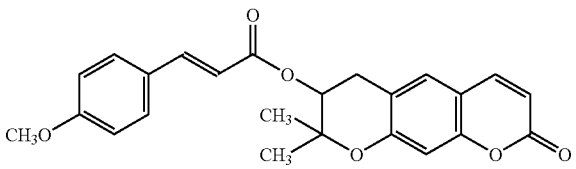

From the above physicochemical properties and spectroscopic results, Compound 3 was identified as 8,8-dimethyl-7-[3-(4-methoxyphenyl)-2E-propenoxy]-2H,6H-benzoyl[1,2-b:5,4-b']dipyran-2-one (IUPAC name; 3-(4-methoxyphenyl)-acrylic acid-2,2-dimethyl-8-oxo-3,4-dihydro-2H,8H-pyrano[3,2-g]cromen-3-yl ester).

Experiment 1: Activity Test of *Angelicae gigantis* Radix Extract (1) Measurement of Cholinesterase Inhibitory Activity AChE inhibitory activity of the methanolic extract and CH$_2$Cl$_2$ fraction of *Angelica gigas* of the above Example 1 was measured by the method of Ellman et al. (Ellman, et al. (1961) A new and rapid colorimetric determination of acetylcholinesterase activity, Biochem. Pharmacol. 7: 88–95).

To a test tube containing a chromogen (5,5-dithiobis-2-nitrobenzoic acid) and a sample was added AChE homogenated with phosphate buffered saline (Electric eel Type V-S, Sigma), and a reaction was performed at 37° C. for 5 minutes, and thereto was added a substrate for the enzyme, acetylcholine iodide, and a reaction was further performed at 37° C. for 3 minutes. Neostigmine bromide was added thereto to terminate the reaction, and then, the absorbance was measured at 412 nm to obtain AChE inhibition (%). The above procedure was repeated with no AChE as a blank, or with no sample as a control. The results are shown in the following Table 1.

TABLE 1

| (concentration: 100 μg/ml) | |
|---|---|
| Fraction | Inhibition (%) |
| Methanolic fraction | 42.1 |
| CH$_2$Cl$_2$ fraction | 49.3 |
| Water fraction | 19.7 |

As shown in the above Table 1, the methanolic extract and CH$_2$Cl$_2$ fraction of *Angelica gigas* according to the present invention had better AChE inhibitory activity than the water fraction.

(2) Passive Avoidance Test

Male ICR mice weighing 25 to 30 g that had been bred with sufficient water and feed in the Experimental Animal Breeding Center of Seoul National University were supplied and adapted to the laboratory environment for 1 week to be used in this experiment.

An avoidance box (40×20×20 cm) equipped with 3 mm stainless steel rod spaced 0.5 cm apart at the bottom was divided into a light compartment and a dark compartment, and when mice placed in the light compartment entered the dark compartment, an electrical shock (0.1 mA/10 g body weight) was delivered through the stainless steel rods. The above procedure was repeated after 24 hours, and the time for which the mice stayed at the light compartment was measured and used as an index of memorizing the training of the previous day. Passive avoidance test was performed according to the method of Christensen et al. (Cholinergic 'Blockade' as a model of the cognitive deficits in Alzheimer's disease, *Brain* 115: 1681–1699, 1992). Specifically, scopolamine was dissolved in physiological saline to 1.5 mg/kg solution, and the solution was subcutaneously injected to mice 30 minutes before the training to induce amnesia. The *Angelica gigas* extract was intraperitoneally injected to the mice 1 hour before the scopolamine administration, and observed for its effect on the scopolamine-induced amnesia. The results are shown in the following Table 2.

TABLE 2

Effect of methanolic extract and CH$_2$Cl$_2$ fraction of *Angelicae gigantis* Radix on passive avoidance in mice with scopolamine-induced amnesia

| Treatment (mg/kg) | | Step-through latency (seconds) |
|---|---|---|
| Saline | | 158.8 ± 27.6 |
| Scopolamine 1.5 | | 29.7 ± 3.1 |
| Scopolamine 1.5 | + AG T 100 | 64.2 ± 7.6*** |
| | + AG C 10 | 48.3 ± 9.3*** |
| | + AG C 50 | 87.9 ± 9.9*** |

AG T: total methanolic extract of *A. gigas*,
AG C: CH$_2$Cl$_2$ fraction of *A. gigas*
The data is expressed as Mean ± S.D., and the significance is ***p < 0.001.

As shown in the above Table 2, the methanolic extract and CH$_2$Cl$_2$ fraction of *Angelica gigas* according to the present invention increased step-through latency in passive avoidance test to have excellent cognition-enhancing activity.

Experiment 2: Activity Test of Decursin and Compound 3 of Example 3

(1) Measurement of Cholinesterase Inhibitory Activity

AChE inhibitory activity of decursin of the above Example 2 and Compound 3 of the above Example 3 was measured according to the method in Experiment 1.

To a test tube containing a chromogen (5,5-dithiobis-2-nitrobenzoic acid) and a sample was added AChE homogenated with phosphate buffered saline (Electric eel Type V-S, Sigma), and a reaction was performed at 37° C. for 5 minutes, and thereto was added a substrate for the enzyme, acetylcholine iodide, and a reaction was further performed at 37° C. for 3 minutes. The above procedure was repeated with no AChE as a blank or with no sample as a control. Neostigmine bromide was added thereto to terminate the reaction, and then, the absorbance was measured at 412 nm to obtain $IC_{50}$ of AChE inhibition. The results are shown in the following Table 3.

TABLE 3

|  | $IC_{50}$ |
| --- | --- |
| Decursin (Compound 1) | $4.8 \times 10^{-4}$ M |
| Compound 3 | $5.1 \times 10^{-5}$ M |
| Decursinol (Comparative Example) | $2.8 \times 10^{-5}$ M |

As shown in the above Table 3, decursin and Compound 3 according to the present invention had better AChE inhibitory activity than decursinol (Comparative Example).

(2) Passive Avoidance Test

Passive avoidance test was performed according to the method of the above Experiment 1(2) to measure effects of pyranocoumarin derivatives of the present invention. Velnacrine (AChE inhibitor) was used as a positive control.

Results for decursin are shown in the following Table 4, and those for Compound 3 are in the following Table 5.

TABLE 4

Effects of decursin (Compound 1) and decursinol (Comparative example 1) on passive avoidance in mice with scopolamine-induced amnesia

| Treatment (mg/kg) | | Step-through latency (seconds) |
| --- | --- | --- |
| Saline | | 172.0 ± 16.0 |
| Scopolamine 1.5 | | 29.7 ± 2.8 |
| Scopolamine 1.5 + | decursinol 1 | 52.1 ± 8.8* |
|  | decursinol 5 | 54.4 ± 10.6* |
|  | decursinol 10 | 43.2 ± 7.7* |
| Scopolamine 1.5 + | decursin 0.5 | 32.1 ± 13.4 |
|  | decursin 1 | 108.6 ± 15.0** |
|  | decursin 5 | 96.5 ± 18.2* |
| Scopolamine 1.5 + | velnacrine 1 | 73.4 ± 6.4** |

The data is expressed as Mean ± S.D., and the significance is *p < 0.05, **p < 0.01.

TABLE 5

Effects of Compound 3 on passive avoidance in mice with scopolamine-induced amnesia

| Treatment (mg/kg) | Step-through latency (seconds) |
| --- | --- |
| Saline | 179.7 ± 0.6 |
| Scopolamine 1.5 | 28.4 ± 10.1 |
| Scopolamine 1.5 + Compound 3 1 | 42.0 ± 17.9 |

TABLE 5-continued

Effects of Compound 3 on passive avoidance in mice with scopolamine-induced amnesia

| Treatment (mg/kg) | Step-through latency (seconds) |
| --- | --- |
| Compound 3 2 | 86.0 ± 18.2*** |
| Compound 3 5 | 171.2 ± 18.7*** |

The data is expressed as Mean ± S.D., and the significance is ***p < 0.001.

As shown in the above Table 4, decursin showed excellent cognition-enhancing activity by remarkably increasing step-through latency in in vivo passive avoidance test, whereas decursinol (Comparative example) did not show such activity.

As shown in the above Table 5, Compound 3 of Example 3 according to the present invention also showed excellent cognition-enhancing activity by remarkably increasing step-through latency in in vivo passive avoidance test.

Hereinafter, formulation examples of the present invention will be described.

| Formulation 1 | |
| --- | --- |
| Decursin | 10 mg |
| Distilled water for injection | q.s. |
| pH adjusting agent | q.s. |

Decursin was dissolved in distilled water for injection, and a pH adjusting agent was added thereto to the pH of about 7.6. Then, the resulting solution was adjusted to the final volume of 2 ml, and then, filled into an ampoule with the volume of 2 ml and sterilized to prepare an injectable solution.

| Formulation 2 | |
| --- | --- |
| Compound 3 of Example 3 | 2 mg |
| Distilled water for injection | q.s. |
| pH adjusting agent | q.s. |

Compound 3 was dissolved in distilled water for injection, and a pH adjusting agent was added thereto to the pH of about 7.2. Then, the resulting solution was adjusted to the final volume of 2 ml, and then, filled into an ampoule with the volume of 2 ml and sterilized to prepare an injectable solution.

| Formulation 3 | |
| --- | --- |
| Methanolic extract of *Angelica gigas* of Example 1 | 10 mg |
| Lactic acid | 100 mg |
| Starch | 100 mg |
| Magnesium stearate | q.s. |

The above ingredients were mixed and the mixture was compressed into tablets according to a conventional method to manufacture tablets.

| Formulation 4 | |
| --- | --- |
| Compound 3 of Example 3 | 10 mg |
| Lactic acid | 100 mg |
| Starch | 50 mg |
| Magnesium stearate | q.s. |

The above ingredients were mixed and the mixture was compressed into tablets according a conventional method to manufacture tablets.

| Formulation 5 | |
| --- | --- |
| Decursin | 5 mg |
| Lactic acid | 50 mg |
| Starch | 50 mg |
| Talc | 2 mg |
| Magnesium stearate | q.s. |

The above ingredients were mixed and the mixture was filled into gelatin capsules according a conventional method to manufacture capsules.

| Formulation 6 | |
| --- | --- |
| Compound 3 of Example 3 | 5 mg |
| Lactic acid | 100 mg |
| Starch | 93 mg |
| Talc | 2 mg |
| Magnesium stearate | q.s. |

The above ingredients were mixed and the mixture was filled into gelatin capsules according a conventional method to manufacture capsules.

| Formulation 7 | |
| --- | --- |
| Compound 3 of Example 3 | 50 mg |
| Sucrose | 20 mg |
| Isomerized sugar | 20 mg |
| Lemon flavor | q.s. |
| Distilled water | ad 100 ml |

The above ingredients were mixed according to a conventional method to manufacture solutions, and the solution was filled into a brown bottle of 100 ml and sterilized to prepare a solution.

| Formulation 8 | |
| --- | --- |
| Decursin | 100 mg |
| Sucrose | 20 mg |
| Isomerized sugar | 20 mg |
| Lemon flavor | q.s. |
| Distilled water | ad 100 ml |

The above ingredients were mixed according to a conventional method to manufacture solutions, and the solution was filled into a brown bottle of 100 ml and sterilized to prepare a solution.

INDUSTRIAL APPLICABILITY

As can be seen from the above, the methanolic extract and $CH_2Cl_2$ faction of *Angelicae gigantis* Radix, decursin (II), and pyranocoumarin derivatives of the above general formula (I) have excellent cognition-enhancing activity, and can be effectively used as an anti-dementia agent.

What is claimed is:

1. A pyranocoumarin compound of the following general formula:

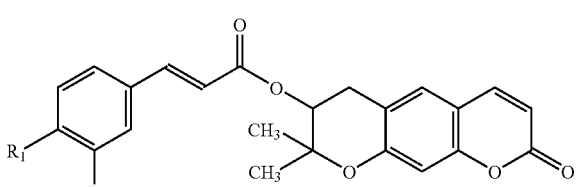

(I)

wherein $R_1$ and $R_2$ each represent hydrogen or $C_{1-4}$ alkoxy, or a pharmaceutically acceptable salt thereof.

2. A pharmaceutical composition for enhancing cognition, comprising a therapeutically effective amount of the compound of the general formula (I) as defined in claim 1 or a pharmaceutically acceptable salt thereof as an active ingredient.

3. A process for preparing the compound of the general formula (I) as defined in claim 1, comprising the step ot which comprises esterifying decursinol of the following formula:

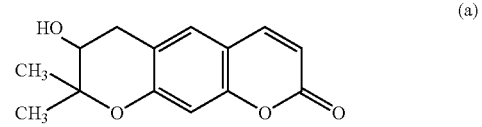

(a)

with a phenyl propanoid of the following formula:

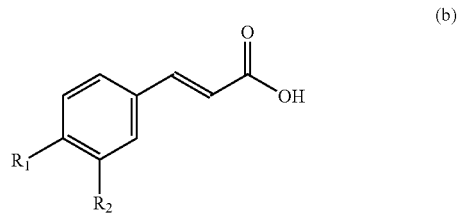

(b)

wherein $R_1$ and $R_2$ each represent hydrogen or $C_{1-4}$ alkoxy, whereby a compound of the general formula (I) is obtained.

4. A method for enhancing cognition in a subject, comprising administering to said subject a therapeutically effective amount of a compound of the following formula (II):

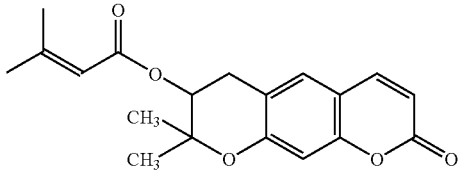

(II)

or a pharmaceutically acceptable salt thereof as an active ingredient, whereby the cognition of the subject is enhanced.

5. A method for enhancing cognition in a subject, comprising administering to said subject a therapeutically effective amount of the compound of formula (I) as defined in claim 1 or a pharmaceutically acceptable salt thereof as an active ingredient, whereby the cognition of the subject is enhanced.

* * * * *